US006419924B1

(12) United States Patent
Sarras, Jr. et al.

(10) Patent No.: US 6,419,924 B1
(45) Date of Patent: Jul. 16, 2002

(54) ANTIBODIES OF ISOLATED DOMAINS OF TYPE IV COLLAGEN MODIFY CELL INTERACTIONS

(75) Inventors: Michael P. Sarras, Jr., Overland Park; Billy G. Hudson, Lenexa, both of KS (US)

(73) Assignee: University of Kansas Medical Center, Kansas City, KS (US)

( * ) Notice: Subject to any disclaimer, the term of this patent is extended or adjusted under 35 U.S.C. 154(b) by 0 days.

(21) Appl. No.: 09/723,602

(22) Filed: Nov. 28, 2000

Related U.S. Application Data

(63) Continuation of application No. 09/183,548, filed on Oct. 30, 1998, now Pat. No. 6,384,012, which is a continuation of application No. 08/800,965, filed on Feb. 18, 1997, now Pat. No. 5,856,184, and a continuation of application No. 08/497,206, filed on Jun. 30, 1996, now Pat. No. 5,691,182, and a continuation of application No. 08/268,969, filed on Jun. 30, 1994, now Pat. No. 5,567,609.

(51) Int. Cl.$^7$ .................. C12N 5/00; A61K 39/395
(52) U.S. Cl. ................ 424/130.1; 530/326; 530/387.1; 530/387.9
(58) Field of Search ............... 530/326, 387.1, 530/387.9; 424/130.1

(56) References Cited

U.S. PATENT DOCUMENTS

| | | |
|---|---|---|
| 5,021,404 A | 6/1991 | Folkman et al. |
| 5,567,609 A | 10/1996 | Sarras et al. |
| 5,691,182 A | 11/1997 | Sarras et al. |
| 5,856,184 A | 1/1999 | Sarras et al. |

OTHER PUBLICATIONS

Ausprunk et al., (1977) *Microvascular Research*, vol. 14, pp. 53–65.
Barzanski et al., (1974) *Amer. Zool.*, vol. 14, pp. 575–581.
Bode et al., (1976) *J. Cell Sci.*, vol. 20, pp. 29–46.
Brooks et al., (1994) *Science*, vol. 264, pp. 569–571.
Butkowski et al., (1985) *J. Biol. Chem.*, vol. 260, pp. 3739–3747.
Butkowski et al., (1987) *J. Biol. Chem.*, vol. 262, pp. 7874–7877.
Carter, (1984) *J. Cell Biol.*, vol. 99, pp. 105–114.
Damsky et al., (1991) *Curr. Opin. Cell Biol.*, vol. 3, pp. 777–778.
Ding et al., (1994) *Kidney Intl.*, vol. 46, pp. 1504–1506.
Dvorak et al., (1987) *Lab. Invest.*, vol. 57, pp. 673–686.
Field et al., (1988) *Science*, vol. 239, pp. 748–752.
Folkman, (1985) *Perspectives in Biol. and Med.*, vol. 29, pp. 10–36.
Gierer et al., (1972) *Nature New Biol.*, vol. 239, pp. 98–101.
Gunwar et al., (1990) *J. Biol. Chem.*, vol. 265, pp. 5466–5469.
Gunwar et al., (1991) *J. Biol. Chem.*, vol. 266, pp. 14088–14094.
Hausman et al., (1971) *J. Exp. Zool.*, vol. 177, pp. 435–446.
Hudson et al., (1993) *J. Biol. Chem.*, vol. 268, pp. 26033–26036.
Hynes, (1987) *Cell*, vol. 48, pp. 549–554.
Hynes, (1992) *Cell*, vol. 69, pp. 11–25.
Ingber, (1990) *PNAS USA*, vol. 87, pp. 3579–3583.
Johansson et al., (1992) *J. Biol. Chem.*, vol. 267, pp. 24533–24537.
Kefalides et al., (1993) *Kidney Intl.*, vol. 43, pp. 94–100.
Kleppel et al., (1986) *J. Biol. Chem.*, vol. 261, pp. 16547–16552.
Kleppel et al., (1989) *Am. J. Pathol.*, vol. 134, pp. 813–825.
Kleppel et al., (1992) *J. Biol. Chem.*, vol. 267, pp. 4137–4142.
Langeveld et al., (1988) *J. Biol. Chem.*, vol. 263, pp. 10481–10488.
Li et al., (1992) *J. of Immunology*, vol. 149, pp. 3174–3181.
Maragoudakis et al., (1993) *Kidney Intl.*, vol. 43, pp. 147–150.
Mariyama et al., (1992) *J. Biol. Chem.*, vol. 267, pp. 1253–1258.
Martin et al., (1988) *Adv. Protein Chem.*, vol. 39, pp. 1–50.
McDonald et al., (1987) *J. Biol. Chem.*, vol. 262, pp. 2957–2967.
McDonald, (1982) *Cell Biol.*, vol. 92, pp. 485–492.
Nayak et al., (1991) *J. Biol. Chem.*, vol. 266, pp. 13978–13987.
Neilson et al., (1993) *J. Biol. Chem.*, vol. 268, pp. 8402–8405.
Nicosia et al., (1990) *Lab. Invest.*, vol. 63, pp. 115–122.
Nicosia et al., (1994) *Exp. Biology*, vol. 164, pp. 197–206.
Ninomiya et al., (1995) *J. Cell Biol.*, vol. 130, pp. 1219–1229.
Oberbaumer et al., (1985) *J. Biol. Chem.*, vol. 271, pp. 9062–9068.
Paku et al., (1991) *Lab. Invest.*, vol. 65, pp. 334–346.
Peczon et al., (1980) *Exp. Eye Res.*, vol. 30, pp. 155–165.
Peissel et al., (1995) *J. Clin. Invest.*, vol. 96, pp. 1948–1957.
Reddy et al., (1993) *Biochem. Biophys. Acta*, vol. 1157, pp. 241–251.
Ries et al., (1995) *J. Biol. Chem.*, vol. 270, pp. 23790–23794.

(List continued on next page.)

*Primary Examiner*—Leon B. Lankford, Jr.
(74) *Attorney, Agent, or Firm*—McDonnell Boehnen Hulbert & Berghoff; David S. Harper

(57) ABSTRACT

The instant invention demonstrates that the 7S domain of type IV collagen disrupts cell aggregation and tissue development. Structural changes in mesoglea, inhibition of cell proliferation, and changes in cell differentiation patterns accompanies the blockage of cell: aggregates which indicate that blockage may be due to alterations in mesoglea (extracellular matrix) structure with accompanying effects on cell behavior. Type IV collagen has a critical role in the initial formation of mesoglea and that perturbation of mesoglea formation affects cell division, cell differentiation, and morphogenesis.

12 Claims, 10 Drawing Sheets

OTHER PUBLICATIONS

Sado et al., (1991) *Virchows Archiv. B Cell Pathol.,* vol. 60, pp. 345–351.
Sado et al., (1995) *Histochem. Cell Biol.,* vol. 104, pp. 267–275.
Sarras et al., (1991) *Dev. Biol.,* vol. 148, pp. 481–494.
Sarras et al., (1991) *Dev. Biol.,* vol. 148, pp. 495–500.
Sarras et al., (1993) *Dev. Biol.,* vol. 157, pp. 383–398.
Sato et al., (1992) *Dev. Biol.,* vol. 151, pp. 111–116.
Saus et al., (1988) *J. Biol. Chem.,* vol. 263, pp. 13374–13380.
Schoefl et al., (1963) *Virehous Arch. Pathol. Anat.,* vol. 337, pp. 97–141.
Shen et al., (1990) *Connective Tissue Res.,* vol. 24, pp. 289–301.
Tagami et al., (1992) *Cell Tissue Res.,* vol. 268, pp. 225–232.
Technau et al., (1992) *Dev. Biol.,* vol. 151, pp. 117–127.
Timpl et al., (1981) *Eur. J. Biochem.,* vol. 120, pp. 203–211.
Timpl et al., (1989) *Int. Rev. Exp. Pathol.,* vol. 29, pp. 1–112.
Tsilibary et al., (1994) *Contrib. Nephrol.,* vol. 107, pp. 70–79.
Varner et al., (1995) *Cell Adhesion and Comm.,* vol. 3, pp. 367–374.
Weber et al., (1984) *Eur. J. Biochem.,* vol. 139, pp. 401–410.
Weber et al., (1992) *Eur. J. Clin. Invest.,* vol. 22, pp. 138–146.
Wieslander et al., (1985) *J. Biol. Chem.,* vol. 260, pp. 8564–8570.
Wood et al., (1980) *J. Ultrastruc. Res.,* vol. 70, pp. 104–117.
Zhang et al., (1994) *Dev. Biol.,* vol. 164, pp. 10–23.

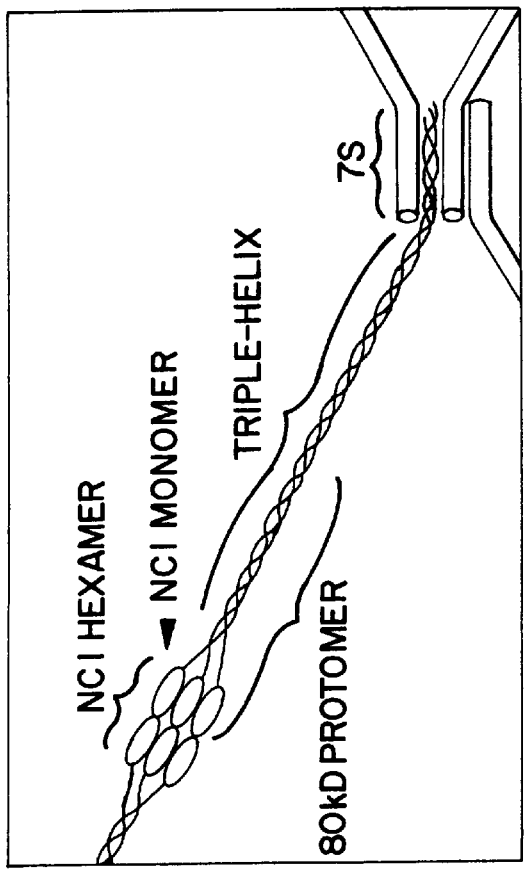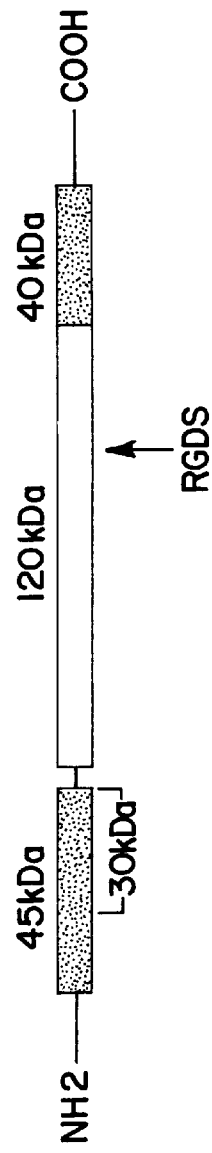
Figure 1a  Type IV Collagen
Figure 1b  Fibronectin

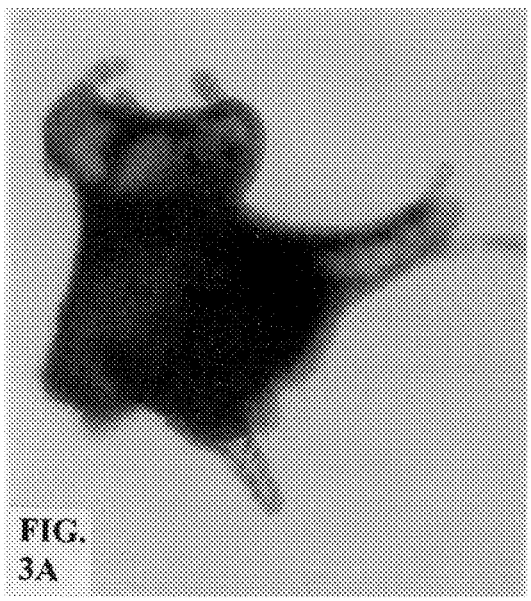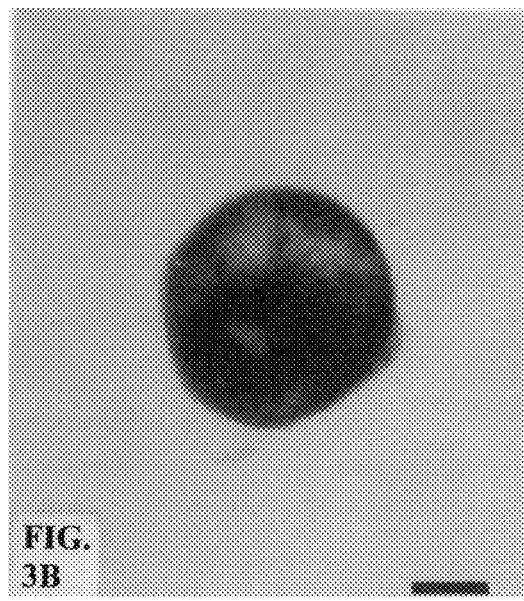
FIG. 3A
FIG. 3B

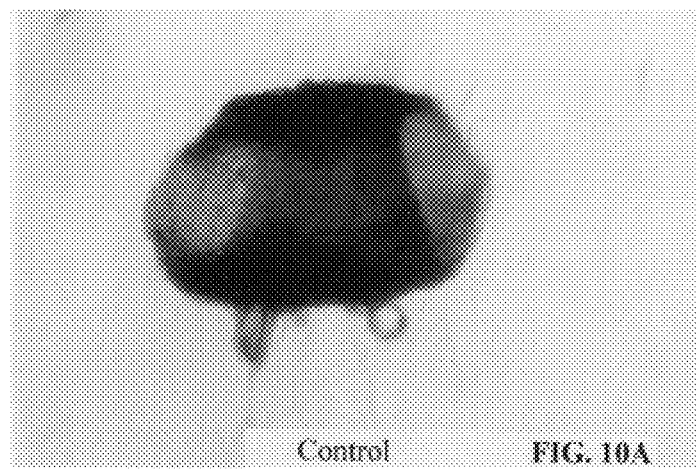
Control  FIG. 10A
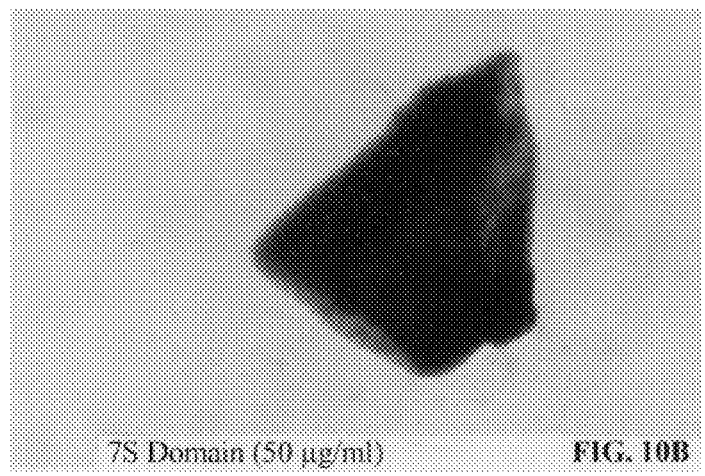
7S Domain (50 µg/ml)  FIG. 10B
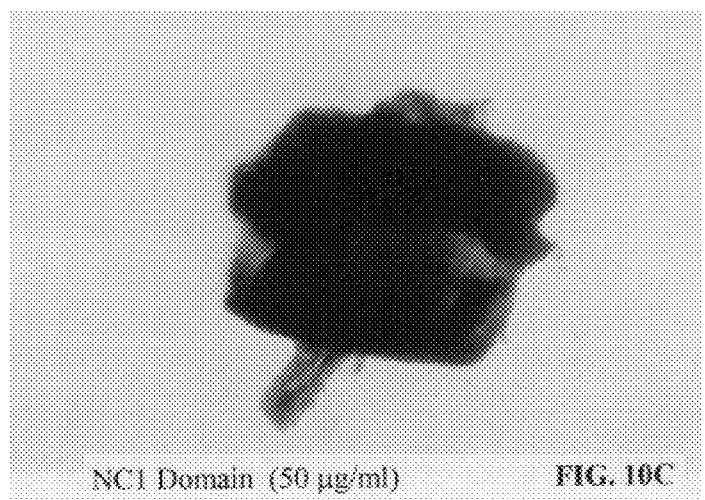
NC1 Domain (50 µg/ml)  FIG. 10C

SEQUENCE LISTING

```
<160> NUMBER OF SEQ ID NOS: 1

<210> SEQ ID NO 1
<211> LENGTH: 4
<212> TYPE: PRT
<213> ORGANISM: Homo sapiens

<400> SEQUENCE: 1

Arg Gly Asp Ser
1
```

ANTIBODIES OF ISOLATED DOMAINS OF TYPE IV COLLAGEN MODIFY CELL INTERACTIONS

This is a continuation of application Ser. No. 09/183,548 Oct. 30, 1998, now U.S. Pat. No. 6,384,012, which is a continuation of Ser. No. 08/800,965, Feb. 18, 1997 now U.S. Pat. No. 5,856,184 and is a continuation of 08/497,206, Jun. 30, 1996, now U.S. Pat. No. 5,691,182 and a continuation of Ser. No. 08/268,969 Jun. 30, 1994 now U.S. Pat. No. 5,567,609.

STATEMENT OF RIGHTS

The U.S. Government has a paid-up license in this invention and the right in limited circumstances to require the patent owner to license others on reasonable terms as provided for by the terms of Grants No. 01-RR06500 and AM 18381 awarded by the National Institute of Health.

BACKGROUND OF THE INVENTION

1. Field of the Invention

This invention relates to methods for the manipulation of in intercellular and intertissue interactions. The instant invention provides methods for the inhibition of cell adhesion to extracellular matrix components or the formation of functional basal lamina, and the manipulation of the results of such attachments. Thus the instant invention pertains to the modification of cellular interactions, with extracellular components, and methods for maintaining cell phenotype, developmental stage, and plasticity in vivo and in vitro.

2. Description of the Prior Art

The basement membrane (basal lamina) is a sheet-like extracellular matrix which is a basic component of all tissues. The basal lamina provides for the compartmentalization of tissues, and acts as a filter for substances traveling between tissue compartments. Typically, the basal lamina is found closely associated with an epithelium, or endothelium in all tissues of an animal including blood vessels and capillaries. The basal lamina components are secreted by cells, and then self assemble to form an intricate extracellular network. The formation of a biologically active basal lamina is important to the development and differentiation of the associated cells.

The Cnidarian, Hydra, is a simplified metazoan whose body wall is composed of an epithelial bilayer with an intervening extracellular matrix (ECM) termed the mesoglea. Hydra mesoglea have been shown to have a number of components seen in the ECM or basement membranes of higher invertebrates and vertebrates, these include: fibronectin, type IV collagen, laminin, and heparan sulfate proteoglycan. Hydra cell aggregation involves the complete morphogenesis of adult hydra from pellets of dissociated hydra cells. During this developmental process, cells segregate into an epithelial bilayer and then deposit a new extracellular matrix prior to the continuation of morphogenesis.

Extracellular matrix (ECM) components play a critical role in development through their affects on such cell processes as cell division, cell attachment, cell migration, and cell differentiation (reviewed by Timpl et al., 1989, Int. Rev. Exp. Pathol. 29:1–112; Damsky and Bernfield, 1991, Current Opn. in Cell Bio. 3:777–778; Hynes, 1992, Cell 69.11–25). It has been established that ECW/cell interactions are utilized by a wide range of vertebrate and invertebrate species to include such primitive organisms as the Cnidarian, Hydra. Hydra is particularly interesting in this regard because it represents one of the first animal phyla to develop defined tissue layers separated by an acellular extracellular matrix (Field et al., 1988, Science 239:748–752). Previous studies have shown that hydra ECM, termed mesoglea, contains type IV collagen, laminin, fibronectin, and heparan sulfate proteoglycans (Sarras et al., 1991a, Dev. Biol. 148:481494). These molecules are continuously synthesized and deposited into the mesoglea in adult hydra and during hydra head regeneration (Hausman et al., 1971, J. Exp. Zool. 177:435–446). Other studies have shown that developmental processes in hydra such as head regeneration are dependent on the normal formation of ECM. These studies have shown that head regeneration in hydra morphogenesis can be blocked by using drugs that perturb collagen cross linking or drugs that interfere with proteoglycan GAG chain extension (Sarras et al, 1991b, Dev. Biol. 1481:495–500). These studies have most recently been extended to the hydra cell aggregate system. This system allows one to form a pellet with dissociated hydra cells and then observe the complete regeneration of the adult hydra body within 72–96 hours through the process of cytodifferentiation and morphogenesis (Gierer et al., 1972, Nature New Biol. 239:98–101; Sarras et al., 1993, Dev. Biol. 157:383–398). Such studies of hydra development and the role of the ECM have focused heavily on a chemical approach (Barzanski et al., 1974, Amer. Zool. 14:575–581; Sarras et al., 1991ab, supra). Hydra cell aggregates first form an epithelial bilayer and then deposit an ECM before morphogenesis proceeds. Hydra cell aggregate development is blocked by drugs that perturb ECM formation and by antibodies raised against isolated hydra mesoglea. These studies demonstrate that functional studies of ECM/cell interaction can be carried out under in vitro conditions with hydra.

Type IV collagen has been shown to be a major structural component of basement membranes and has also been shown to be present in hydra ECM. The protomeric form of type IV collagen is formed as a heterotrimer made up from a number of different subunit chains called $\alpha 1(IV)$, $\alpha 2(IV)$ etc. The type IV collagen heterotrimer is characterized by three distinct structural domains: the non-collagenous (NC1) domain at the carboxyl terminus; the triple helical collagenous domain in the middle region; and the 7S collagenous domain at the amino terminus (FIG. 1) (Martin et al., 1988, Adv. Protein Chem. 39:1–50; Gunwar et al., 1991, J. Biol. Chem. 266:14088–14094). Type IV collagen exists as a supramolecular structure in ECM and this structure is thought to serve as a framework which provides mechanical stability to ECM (Timpl et al., 1986, supra) and as a scaffolding for the binding and alignment of other ECM molecules such as fibronectin, laminin, eutectin, and heparan sulfate proteoglycans (Gunwar et al., 1991, supra). The biological function of type IV collagen is critically related to the formation of an intact ECM since disruption of collagen cross linking by β-aminopropionitrile interferes with the mesoglea formation and this leads to a blockage in normal hydra morphogenesis (Sarras et al., 1991b. 1993, supra).

Hydra cell aggregate development involves complete morphogenesis of adult hydra structures within 96 hr from pellets formed with dissociated hydra cells (Grierer et al., 1972, supra; Sato et al., 1992, Dev. Biol 151:111–116; Technau et al., 1992, Dev. Biol. 151:117–127; Sarras et al., 1993, supra ). Morphologically, hydra cell aggregate development can be divided into two stages. The initial stage is from Time 0 to 24 hr when aggregates develop from a solid cell mass into a fluid-filled cyst where the outer wall is formed from an epithelial bilayer with an intervening ECM termed mesoglea. This stage involves active cell sorting between ectodermal and endodermal cells (Technau et al., 1992, supra) and subsequent mesoglea formation once the bilayer is established. The later developmental stages (24–96 hr) involve processes normally associated with tissue histogenesis; namely, alterations in the shape of epithelial layers, cell migration, cell differention, and other processs that result in morphogenesis of foot, head, and tentacle structures. In regard to the initial stages of hydra cell aggregate development, it has been shown that head regeneration in aggregates is not due to the clustering of cells from the original head regions. It has been suggested that head regeneration arises de novo (Gierer et al., 1972, supra; Technau et al., 1992, supra) from foci of developmental gradients established around the spherical aggregate. This indicates that cell differentiation or transdifferentiation into head region cells actively occurs during hydra cell aggregate development. In addition to positional information and possible activator influences, cells may differentiate or transdifferentiate under the influences of other developmental cues such as signals arising from the ECM.

Previous studies have shown that in vertbrates, fibronectin interacts with various collagens during matrix assembly, including type IV collagen (Carter, 1984, J. Cell Bio. 99:105–114). In addition, antibodies to the collagen binding domain of fibronectin had the ability to block ECM assembly by human lung fibroblasts. (McDonald. 1982, J. Cell Biol. 92:485–492). Other studies raised doubts as to the interaction, while polyclonal antibodies to the collagen binding domain blocked matrix assembly, purified collagen binding domains had no inhibitory effects in this assembly process (McDonald et al., 1987, J. Biol. Chem. 262:2957–2967; Hynes, 1990, Cell 48:549–554). In general fibronectin (FN) appears before collagen during assembly of vertebrate matrices, however, in the case of hydra ECM formation, FN and collagen appear in the mesoglea about the same time, based on immunofluorescent studies. Type IV collagen has been implicated as important in several human diseases (Hudson et al., 1993, J. Biol. Chem. 268:26033–26036). Basement membrane and its components have a role in lymphocyte adhesion, migration and proliferation (Li and Cheung, 1992, J. of Immunology 149:3174–3181).

The fundamental role ECM plays in tissue development and cell differentiation reverberates across phyla and kingdoms, to focus attention on the most basic elements that are required for all tissue interactions. The use of hydra as a model system for the study of basic elements of complex tissue interactions is a recognized approach. Instead of attempting to deduce the interaction between isolated tissues of higher order animal, the same mechanisms and phenomenon can be examined in vivo by using the complete animal, in hydra. This approach has led to the use of hydra to study the effects of glucose on tissue morphology, in an effort to understand the pathological effects of uncontrolled diabetes on kidney glomeruli, with excellent results (Zhang et al., 1990, Diabetologia 33:704–707).

Recently the β1-laminin gene has been cloned and sequenced in hydra, showing very high homology with the human counter part. The homologues of fibronectin and collagen are present as well. It is a reflection on the fundamental role ECM plays, that hydra and higher order animal show the same cell matrix interactions, with similar components, domain interactions, receptor molecules and response to extracellular signals. Mammalian, and even human hormones, when applied to hydra result in bioactivity and effects on cell behavior. It is possible to use human insulin to stimulate cell proliferation in hydra. Other such cross-phyla activities can be attributed to many growth factors as well, i.e. EGF (epidermal growth factor), TGF-β, FGF (fibroblast growth factor), PDWF, to name a few.

Specific methods, for the manipulation of cell adhesion to ECM, basal lamina, or adjacent cells would be useful for the in vivo manipulation of tissues and cells. Methods which address the fundamental elements of basic cell and tissue interactions are applicable to all systems which exhibit similar characteristic features. Such in vivo uses include, and are not limited to, inhibition of basal lamina formation, inhibition of basal lamina/cell interactions, and to encourage cells to maintain phenotypic plasticity. Such methods will also be useful for the in vitro manipulation of cells and tissues, for instance in maintaining cell cultures in undifferentiated or homeostatic states, non-enzymatic dispersal of cells from attachments, or the maintenance of confluent cells in suspension for propagation, maintenance, or collection.

SUMMARY OF THE INVENTION

The instant invention provides methods for inhibiting basal lamina membrane formation, in cell or tissue development, comprising contacting the cell or tissue with one or more isolated domains of type IV collagen. The instant invention also provides methods for in vitro cultivation of cells comprising contacting the cells to be cultivated with an isolated domain of type IV collagen to disrupt the formation of basal or extracellular matrix contacts. The instant invention further provides methods for disrupting basal lamina membrane formation in tissues comprising contacting the tissues with an isolated domain of type IV collagen. In a specific embodiment of the instant invention, the isolated domain of type IV collagen is the 7S or NC1 domain, or protein constructs having substantially the same structure as the active elements within the 7S or NC1 domain.

Thus the instant invention provides methods for the interference with cell interactions with basal lamina components which comprises contacting the cells or tissues with an isolated domain of type IV collagen, and in a preferred embodiment the isolated domain is either the 7S domain or the NC1 domain of type IV collagen or substantially homologous protein constructs thererof which contain the specific structural elements within the 7S and NC1 domain that convey activity.

BRIEF DESCRIPTION OF THE DRAWINGS

FIG. 1 are two diagrams illustrating segments of type IV collagen (IA) and fibronectin proteolytic fragments (1B) used in blocking experiments.

FIG. 3 are photographs of representative Hydra cell aggregates at 96 hr of development. Control aggregates develop head and tentacle structures (3A) while blocked aggregates remain in the characteristic 24-hr cystic stage (3B). Bar=286 μm.

FIG. 10 are photographs of mouse thoracic aorta segments embedded in Matrigel (EHS basement membrane matrix, Collaborative Biomedical Products, Bedford, Mass.) at 5 days of culture. Control specimen (0 ug/ml of NC1 (Hexamer) and 7S domains) exhibited growth of microvessels from the cultured tissue into the matrix (FIG. 10A). In contrast, angiogenesis was inhibited in specimens cultured with 50 ug/ml of 7S domain (FIG. 10B) and NC1 (Hexamer) domain (FIG. 10C).

DESCRIPTION OF THE PREFERRED EMBODIMENTS

Figure 2:
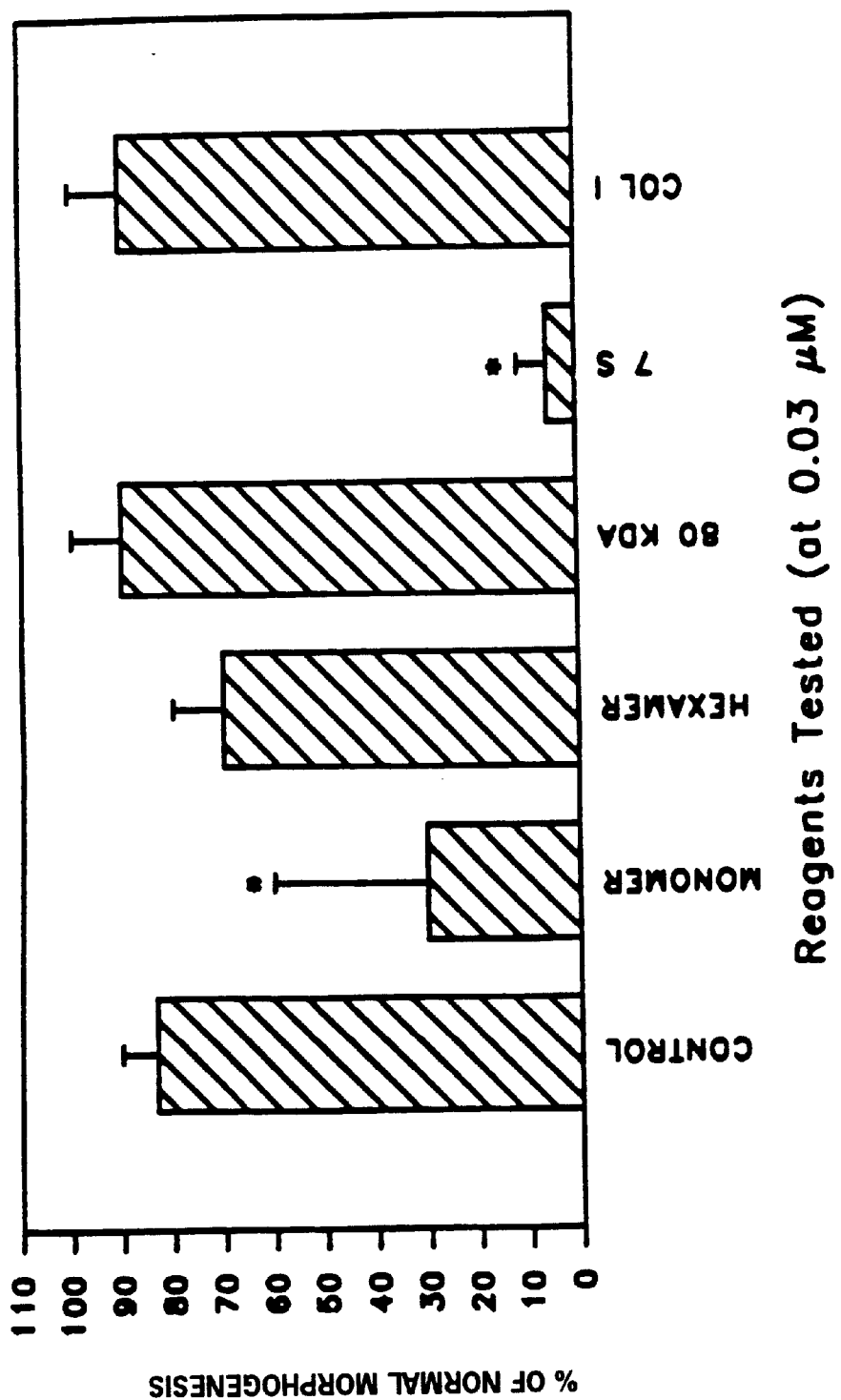
FIG. 2 is a graph which illustrates results of the blockage of aggregate morphogenesis observed with NC1 domain monomer and 7S domain, when all type IV collagen fragments are compared on an equal molar basis (0.03 μM). From left to right: control group; NC1 monomer; NC1 hexamer; 80-kDa fragment of NC1; 7S domain; type I collagen. Results are reported as % of normal morphogenesis as described below.

Our studies indicate that the formation of an appropriate ECM structure involving fibronectin and type IV collagen is critical to cell aggregate development and that perturbation of ECM formation adversely affects cell division and cell differentiation during the formation of complex cell aggregations and tissues. This is illustrative of the critical role the ECM and cell-ECM interactions play in tissue development in all organisms that have differentiated tissues. Structural changes in mesoglea, inhibition of cell proliferation, and changes in cell differentiation patterns accompanied the blockage of cell aggregates. Thus type IV collagen is critical to the early stages of cell aggregate development when the mesoglea is initially formed and that perturbation of aggregate development by fragments of type IV collagen results in alterations in hydra cell division, cell differentiation, and morphogenesis. It is demonstrated that type IV collagen components are critical element in the formation of any cell to ECM (basal lanmina) contacts, and that by applying the proper methods, this interaction can be manipulated in a predictable fashion.

The following examples are meant to illustrate specific embodiments of the instant invention, and are in no way intended to limit the breadth or scope of the teachings embodied in the instant specification. One with ordinary skill in the art will be able to take the teachings of the instant specification and use the instant invention in other specific embodiments.

EXAMPLE 1

Disruption of Cell Aggregate Development

All experiments utilized *Hydra vulgarie* (previously named *Hydra attenuata*). Animals were cultured as described previously (Sarras et al., 1991a, supra) and were not fed for 24 hr prior to use.

Hydra cell aggregates were prepared according to Gierer et al., (1972, supra) with modifications described by Sarras et al. (1993, supra). They were incubated either in microtiter plates (NUNS, Denmark) with one aggregate/well/10 µl incubation solution or in 96-well plates (Falcon) with three to five aggregates/well/50 µl incubation solution. Antibiotics were used throughout all steps of aggregate preparation to assure that the aggregates used in this study were free of any symbionic bacterial populations (Sarra et al., 1993, supra). Various analysis indicated that aggregates were free of bacteria under these conditions. By 24 hr of Cell pellet formation hydra cell aggregates develop separate junctions between epithelial cells (Wood et al., 1980. J. Ultrastruc. Res. 70:104–117). These junctions prevent the introduction of macromolecules from medium into mesoglea. Therefore, exogenous matrix probes, (e.g., fibronectin, type IV collagen, and type IV collagen fragments, peptides or antibodies) were added to the culture medium immediately after pellet formation (Time 0). Control hydra cell aggregates were cultured in hydra medium, bovine serum albumin (Sigma, St. Louis, Mo.), or nonimmune serum. After 24 hr of incubation, aggregates (both control and experimental groups) were transferred into fresh hydra medium and culture was continued until 96 hr.

Type IV collagen fragments used in blocking experiments are illustrated in FIG. 1 (A). The NC1 monomer—a mixture of α1(IV), α2(IV); NC1 hexamer; 80-kDa protomeric truncated fragment (NC1 domain with part of triple helix); and the 7S domain, were all obtained from enzymatic digestion and subsequent chromatographic purification of bovine kidney glomeruli basement membrane or bovine lens basement membrane (Langeveld et al., 1988, J. Biol. Chem. 263: 10481–10488; Gunwar et al., 1991, supra). Antibody to the NC1 (α1(IV)+α2(IV)) domain of type IV collagen was generated in rabbits immunized with monomeric subunits isolated from the globular domain of bovine kidney basement membrane type IV collagen (Langeveld et al., 1988, supra). The precise molar concentrations of these fragments was determined by spectrophotometry and amino acid composition analysis.

Criteria for morphogenesis was as follows. The morphological development of hydra cell aggregates was studied using a dissecting microscope (Wild, Herbrugg). Observations were carried out at Time 0, 24, 48, 72, and 96 hr. The normal morphogenesis of hydra cell aggregates between Time 0 and 96 hr has been described previously by Gierer et al., (1972, supra) and Sarras et al., (1993, supra). Abnormal development (blockage) of hydra cell aggregates was considered if an aggregate did not show head and tentacle structures at 96 hr, i.e., was retained in a cystic stage (FIG. 3). The percentage of aggregates with head and tentacle structures at 96 hr of development was calculated and data for each group from different experiments were pooled and plotted. A minimum of five aggregates were tested per group and all experiments were repeated at least three times except where indicated. Using an ANOVA statistical test, a P value <0.05 was taken as the level of significant difference in all groups analyzed. The ANOVA statistical test was used for all data analysis.

Transmission electron microscopy was used to examine the fine structure and morphology of control and treated aggregates. Cell aggregates were immersed in Karnovsky's fixative overnight at 4° C. and postfixed in 1% $OsO_4$ for 1 hr. Samples were then stained en bloc in 0.5% uranyl magnesium acetate overnight at 4° C. After dehydration and infiltration, samples were embedded in Spur's resin. Blocks were cut with a Reichert-Jung microtome, stained with uranyl acetate and lead citrate, and viewed using a JOEL 100S transmission electron microscope. Morphometry analysis was carried out as described previously (Zhang et al., 1990. supra).

Immunofluorescent screening for type IV collagen in hydra cell aggregates at various time points after pellet formation showed that signal was detected at 48 hr, and became progressively stronger and remained in the mesoglea throughout all later stages of aggregate development. FIG. 3 illustrates the typical appearance of control and blocked aggregates at 96 hr. Blocked aggregates failed to develop beyond the 24 hr stage, and either remaining in a cystic stage or disaggregating into dissociated cells by 96 hr.

Figure 4:
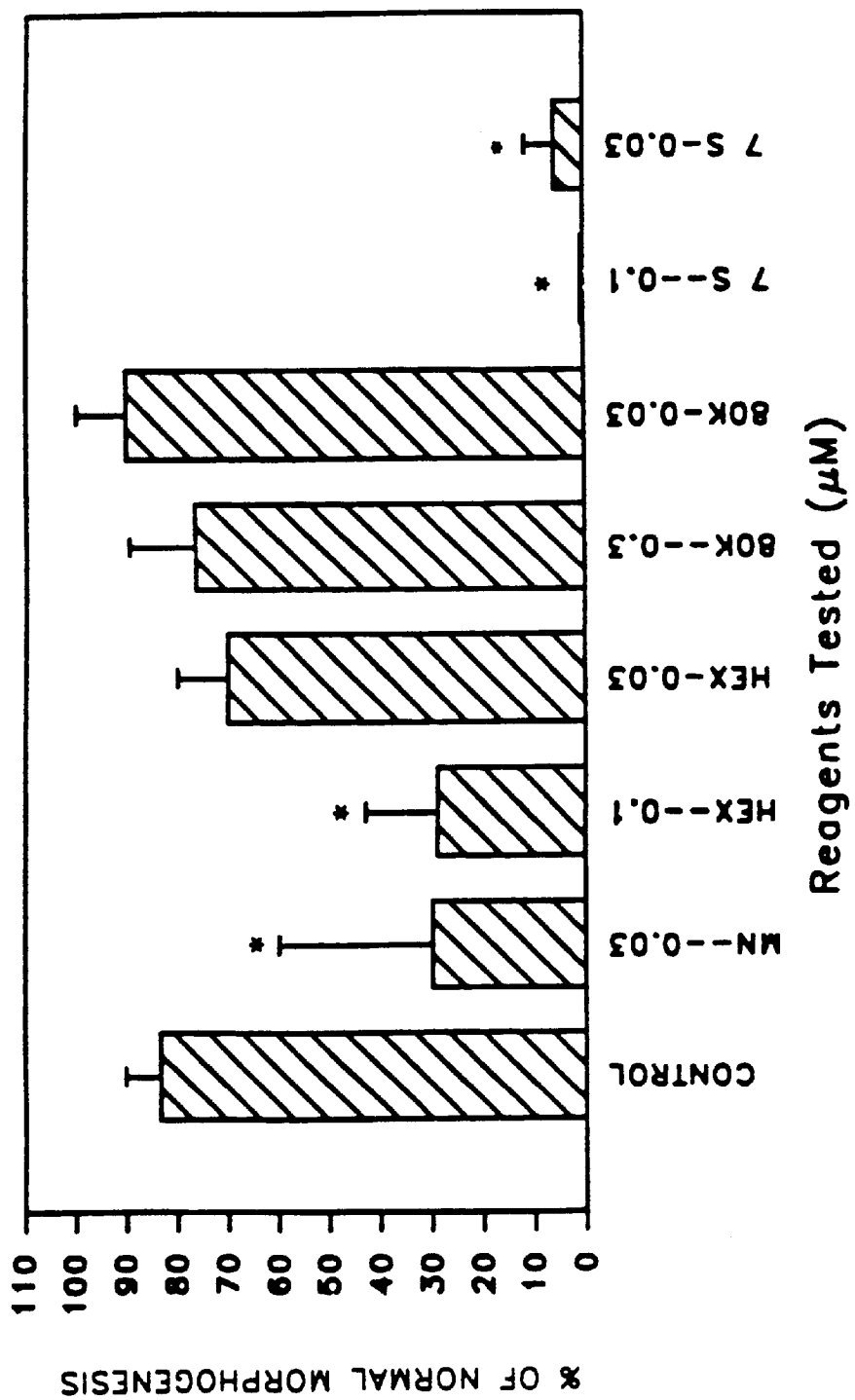
FIG. 4 is a graph which illustrates the concentration effect of the various blocking agents. At higher concentrations, NC1 domain hexamer also showed blocking effects, whereas no blockage was observed with the 80-kDa fragment of NC1. From left to right: control group; NC1 monomer (MN) at 0.03 µM; NC1 domain hexamer (HEX) at 0.1 µM; NC1 domain hexamer (HEX) at 0.03 µM; NC1 domain 80-kDa fragment (80K) at 0.3 µM; NC1 domain 80-kDa fragment (80K) at 0.03 µM; 7S domain (7S) at 0.1 µM; and 7S domain (7S) at 0.03 µM. Results are reported as % of normal morphogenesis as described below.

As shown in FIG. 2, the 7S domain, and monomers of NC1 domain were most effective in blocking hydra cell aggregate morphogenesis when fragments were tested on an equal molar basis. This blockage was also concentration dependent NC1 hexamer blocked aggregate development at higher concentrations whereas the 80-kDa fragment showed no effect (FIG. 4). Antibody to NC1 domain had a similar blocking effect (Table 1).

TABLE 1

Treatment with Antibody to ECM Components

| Treatment | % of normal morphogenesis |
| --- | --- |
| nonuniform serum 1:10–1:100 | 79 ± 7.25 (54/68)[a] |
| Anti-NCl 1:10[b] | 0 (0/15) |
| Anti-NCl 1:40 | 0 (0/6) |
| Anti-NCl 1:80 | 100 (3/3) |
| Anti-FN 1:10[c] | 0 (0/15) |
| Anti-FN 1:50 | 0 (0/12) |
| Anti-FN 1:100 | 32 ± 15.5 (10/30) |
| Anti-FN 1:200 | 33 ± 19.25 (5/15) |

[a]Data are presented as means ± SEM (No. with normal morphogenesis/total No. treated).
[b]Polyclonal Ab against NCl (α1(IV) + α2(IV)) domain of bovine kidney type IV collagen.
[c]Polyclonal Ab (ICN Biochemicals) against human plasma fibronectin.

Figure 6:
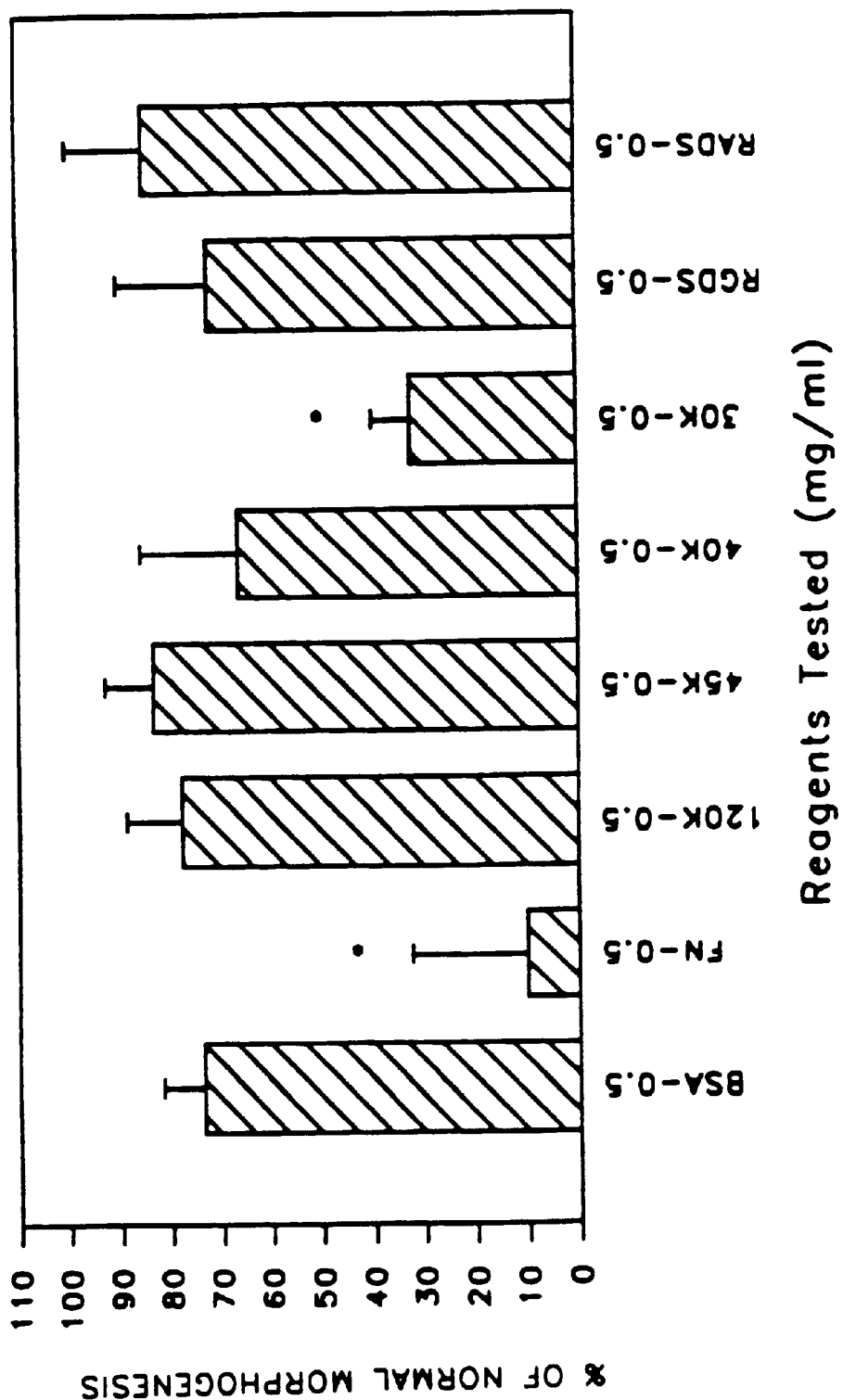
FIG. 6 is a graph which illustrates the results of the block of aggregate formation using fibronectin and fibronectin derived proteolytic fragments. All samples were tested at 0.5 mg/ml. From left to right: BSA (Bovine Serum Albumin); FN (intact fibronectin); 120K (the 120-kDa fragment of FN); 45K (the 45-kDa fragment of FN); 40K (the 400-kDa fragment of FN); 30K (the 30-kDa fragment of FN); RGDS (RGDS peptide); RADS (RADS peptide). Results are reported as % of normal morphogenesis as described below. The effectiveness of the blocking agents was found to be concentration dependent.

Similar studies were carried our using fibronectin as the inhibitor. Intact fibronectin, proteolytic fragments, RGDS peptides, and antibody to fibronectin were tested to determine their effect on hydra cell aggregate development. FIG. 1(B) shows a diagram of the relationship of the various fragments to the intact fibronectin molecule. Of these, intact fibronectin and its 30-kDa gelatin binding domain were found to be effective at 0.5 mg/ml in blocking aggregate development (FIG. 6). Effectiveness was found to be concentration dependent. Antibodies against fibronectin also showed blocking effects (Table 1).

Figure 5A:
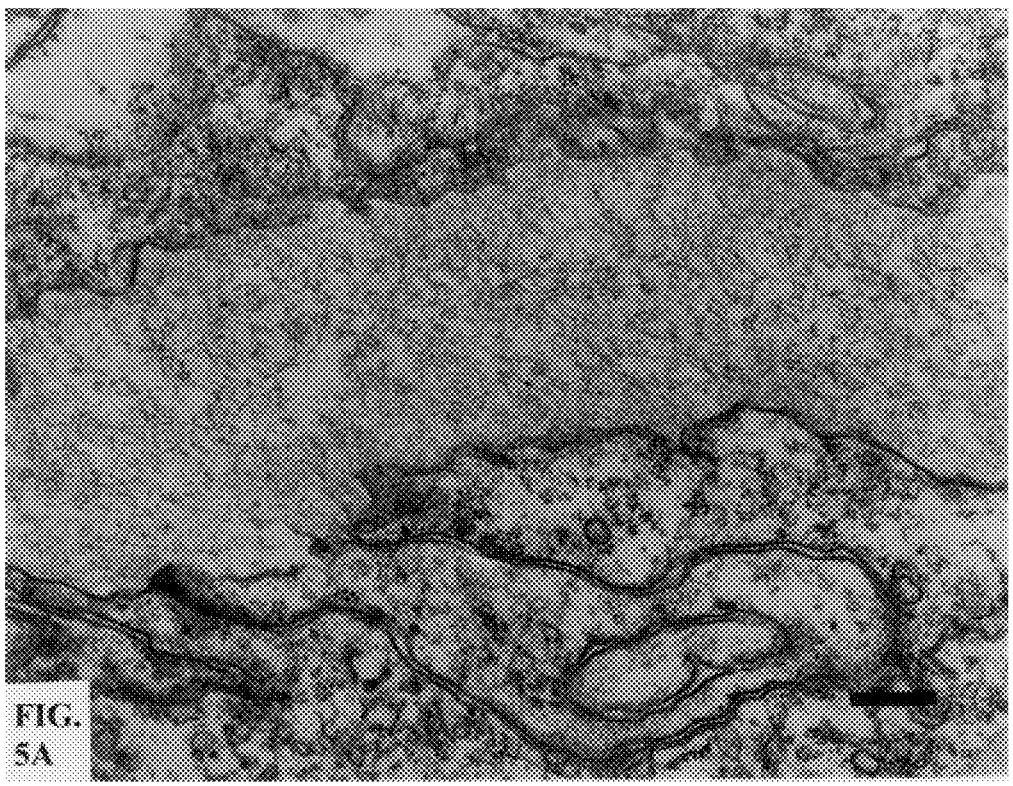
FIG. 5 are electron micrographs showing representative morphology of control (5A) and blocked (5B) aggregate cells.
Figure 5B:

Transmission electron microscopy was used to study the ultrastructure of mesoglea under the influences of each exogenously introduced ECM molecule. Blocked aggregates were processed for TEM analysis at various time points of experiments and the ultrastructure of their mesoglea was compared to that of control aggregates fixed at the same time of development. As compared to control group specimens (FIG. 5A), the ultrastructure of mesoglea in blocked aggregates was reduced in thickness, irregular at its epithelial border, and appeared to have lost some of its normal ultrastructural organization (FIG. 5B). Morphometric analysis (Table 2) indicated that the mesoglea of blocked aggregates was reduced in thickness by approximately 50% compared to controls and this reduction was significant as determined using statistical analyses. This altered mesoglea ultrastructure was observed with all blocking reagents tested.

TABLE 2

Morphometric Analysis

| Treatment (from Time 0 to 24 hr) | Interepithelial width of mesoglea as reflected by area measurements[a] |
| --- | --- |
| BSA[b] | 1434 ± 582 |
| 30 kDa[c] | 724 ± 245* |
| Anti-FN[d] | 969 ± 458* |

[a]All EM micrographs of mesoglea were taken at 8.000× magnification and printed at the same size. An 80-mm section was bracketed along mesoglea on each print and mesoglea within the bracketed area was measured by computer program, SigmaScan. The measuring unit is $mm^2$. Under these measuring conditions, area reflects interepithelial width changes as previously described (Zhang et al., 1990, supra). Data are represented as mean ± SD.
[b]Bovine serum albumin at 0.1 mg/ml concentration.
[c]Fibronectin 30-kDa gelatin binding fragmetn at 0.1 mg/ml.
[d]Antibody to fibronectin at 1:100 dilution.
*Statistically different from BSA group (P value <0.05).

To determine if inhibition of cell proliferation was responsible for the blockage of cell aggregate morphogenesis, aggregates were treated from Time 0 to 96 hr with 10 μM hydroxyurea (HU), which has been shown to inhibit DNA synthesis in hydra cells (Bode et al., 1976, J. Cell Sci. 20:29–46). Although HU completely blocked DNA synthesis, the drug did not inhibit morphogenesis of hydra cell aggregates.

A critical role for collagen in the process of matrix formation follows from previous pharmacological studies involving lanthrytic agents (Barzanski et al., 1974, supra; Sarras et al., 1993, supra). In the present demonstration, type IV collagen domains were effective in perturbing mesoglea formation and in blocking aggregate development. In this regard, the NC1 domain monomer and the 7S domain fragment were most effective in blocking aggregate development when all type IV collagen fragments were compared on an equal molar basis. Others have proposed that the NC1 domain and the 7S domain are the sites at which the type IV collagen protomer is involved in intermolecular bridging during formation of the supramolecular network (Martin et al., 1988, Adv. Protein Chem. 39:1–50).

It is not clear why the larger NC1 hexamer and the 80-kDa fragment were less effective than the smaller NC1 monomer in blocking development. The same phenomenon was seen with fibronectin, while the most effective blocker, the 7S fragment, has a mass greater than 100 kDa. On a total mass basis, the 7S domain has a relatively high proportion of carbohydrate residues associated with the polypeptide chain (15–18%), and further analysis of these carbohydrate residues indicate that they have unique structural features such as the presence of terminal α-D-Gal residues on N-linked oligosaccharide groups. (Langenveld et al., 1991, supra; Nayak et al., 1991, J. Biol Chem. 266:13978–13987). The inability of type I collagen to block development is consistent with the fact that it has not been detected in hydra mesoglea.

The effect of mesoglea components on hydra cell behavior may be viewed at two levels. At one level, mesoglea may be viewed as simply a structural entity which is required as a foundation for stability and maintenance of the epithelial bilayer. At another level, however, ECM components in mesoglea provide developmental cues which modulate such cell processes as cell division, migration, and differentiation during hydra morphogenesis. It is clear that ECM components are not simply structural molecules. Fibronectin and type IV collagen have been shown to control endothelial cell proliferation and differentiation (Tagami et al., 1992, Cell Tissue. Res. 268:225–232; Ingber, 1990, PNAS USA 87:3579–3583). It has been shown that the mechanochemical interactions between striated muscle cells in jellyfish and grafted mesoglea can induce or inhibit DNA replication and cell transdifferentiation. In the present examples, while cell proliferation is inhibited in morphologically blocked aggregates, it is also apparent that normal aggregate morphogenesis can occur even in the absence of cell proliferation. Therefore, a reduction of cell division in blocked aggregates can not account for the blockage observed in aggregate morphogenesis.

The homology between the hydra model system and what is known about the developmental and regulatory mechanisms of higher organisms makes the use of type IV collagen fragments in this system applicable to the same cell and tissue interactions in other organisms. The instant methods are applicable to, among other things, the inhibition of metastasis, control of cell division, reduction of scar tissue formation, intervention in epithelial tissue formation, inhibition of angiogenesis, reduction of complications due to cell adhesion in organ transplants, inhibition of angiogenic invasion of tissue, or the inhibition of lymphocyte adhesion and mobility.

EXAMPLE 2

Cell Culture Maintenance

The methods of the instant invention are quite useful for the maintenance of cells in culture, where such maintenance requires maintenance of cell phenotype and morphology with minimal adhesion. It is well recognized that there are many critical factors that contribute to the successful maintenance and propagation of cells in culture. Namely cell division can be anchorage dependent, and in some instances will show density-dependent inhibition. Generally most cultures made from cells dissociated from tissues, unlike bacteria, are not adapted to living in suspension and require a solid surface on which to grow and divide. Cells are now grown in cultures, so that they adhere to plastic. Cells can vary in the requirements of culture media, and the nature of the supports aid some cells will not grow without the proper ECM components coated on the plastic dish. Recognized methods for mammalian cell culture can be found in such general references as "Mammalian Cell Biotechnology," edited by M. Butler, Oxford University Press, 1991, and "Readings in Mammalian Cell Culture," 2nd Edition, edited by R. Pollack, Cold Spring Harbor Laboratory, 1981.

The methods of the instant invention will provide a means by which the requirement for adhesion is eliminated by providing the cells with an effective amount of the type IV collagen domains which will allow the cells to remain in solution while still appearing to be bound to ECM. This will greatly improve the use of cell cultures in bioreactors and other large scale commercial applications. The use of NC1 or 7S domain in about the same effective concentration per cell as demonstrated in the previous example will keep cultures of cells effectively bound without adhesion. Further, isolation and manipulation of cells will not require the use of general pharmacological agents which effect many cellular function in an imprecise and non-specific manner.

Primary cultures, those isolated directly from animal tissues, can be used to form secondary cultures of specific cells. In this manner, the cells can be subcultured for several weeks or months displaying the phenotype and morphology of the parent cells. Most vertebrate cells will die in culture after a finite number of divisions, for example human skin cells can typically last for several months dividing from 50 to 100 times before they die. Variant cell lines can arise, however, which are immortal in that they can be propagated in cell culture indefinitely. These cells usually grow best when attached to a solid support, and typically will cease to grow once they have formed a confluent layer on the surface, demonstrating contact inhibition. Cell lines prepared from cancer cells differ from those prepared from normal cells in many ways. Such cells tend to proliferate without solid support and will grow to much greater density than normal cells.

Thus the methods of the instant invention can be used to affect primary and secondary cell cultures so that they behave as if in contact with a solid support, but without the effects of cellular contact inhibition. Thus parent cell lines can be maintained in vitro under conditions that will promote the maintenance of cell phenotype and morphology.

One area of great interest is the isolation and culture of embryonic or pluripotent stem cells in vitro for eventual manipulation and use in vivo. The isolation and maintenance of such relatively undifferentiated cells, and the propagation of such cells would allow for the production of vast amounts of specific cells which could form the basis of tissue regeneration or replacement. Thus the teachings of the instant invention can be applied to the maintenance of pluripotent cell isolates and allow for die propagation of these cells while inhibiting morphological change and differentiation in vivo.

EXAMPLE 3

In Vitro Effect on Angiogenesis

Angiogenesis, the process of formation of new blood vessels, plays an important role in physiological processes such as embryonic and postnatal development as well as wound repair. Formation of blood vessels can also be induced by pathological processes involving inflammation (e.g., diabetic retinopathy and arthritis) or neoplasia (e.g., cancer) (Folkman, 1985, Perspect. Biol. Med., 29, 10). Neovascularization is regulated by angiogenic growth factors secreted by tumor or normal cells as well as the composition of the extracellular matrix and by the activity of endothelial enzymes (Nicosia and Ottinetti, 1990, Lab. Invest., 63, 115).

During the initial stages of angiogenesis, endothelial cells sprouts appear through gaps in the basement membrane of preexisting blood vessels (Nicosia and Ottinetti, 1990, supra; Schoefl, 1963, Virehous Arch. Pathol. Anat. 337, 97–141; Ausprunk and Folkman, 1977, Microvasc. Res. 14, 53–65; Paku and Paweletz, 1991, Lab. Invest. 63, 334–346). As new vessels form, their basement membrane undergoes complex structural and compositional changes which are believed to affect the angiogenic response (Nicosia et al., 1994, Exp. Biology, 164, 197–206). Early planar culture models have shown that basement membrane molecules modulate the attachment, migration and proliferation and organizational behavior of endothelial cells (Nicosia et al., 1994, supra). More recent studies with three-dimensional aortic culture models which more closely simulate angiogenic conditions that occur during wound healing in vivo suggest that basement membrane is a dynamic regulator of angiogenesis whose function varies as to its molecular components (Nicosia, 1994, supra).

With modifications, the procedures of Nicosia and Ottinetti (1990), supra, and Nicosia et al (1994), supra, were utilized for experiments designed to test the effect of Type IV collagen on angiogenesis under in vitro conditions. The model has used to study the effects of growth factors and extracellular matrix molecules on the angiogenic response and employs aortic rings cultured in three-dimensional collagen gels under serum-free conditions. These experiments are outlined below.

A. Methods

Experiments were performed with Swiss Webster male mice which were 1 to 3 months old. Following anesthesia, the thoracic aorta was excised under aseptic conditions and transferred to sterile MCDB 131 sterile growth medium (Clonctics, San Diego, Calif.) containing antibiotics. Fat was dissected away from the aorta and approximately six to eight 1 mm thoracic segments were obtained from each specimen. Segments were transferred to 48 well tissue culture plates. The wells of these plates were layered with 100 microliters of Matrigel (EHS basement membrane, Collaborative Biomedical Products, Bedford,. Mass.) prior to transfer of the aortic segments. The Matrigel was diluted 1:1 with MCDB 131 growth medium prior to use. The segments were centered in the wells and an additional 100 microliters of Matrigel was then placed over the specimens. The aortic segments were therefore embedded in the basement membrane matrix. Each well then received 300 microliters of MCDB 131 growth medium. The plates were placed in an incubator maintained at 37° C. with 5% $CO_2$. Specimens were observed daily over a 7 day period. Newly growing microvessels were counted using an inverted phase microscope at various times during the culture period, but data is expressed at 3 and 5 days of culture. To test for the effect of Type IV collagen on angiogenesis, domains at known concentrations are mixed with the Matrigel and with the MCDB 131 growth medium. Fresh MCDB 131 growth medium (plus and minus collagen domains) was changed every 3 days.

B. Results

Figure 7:
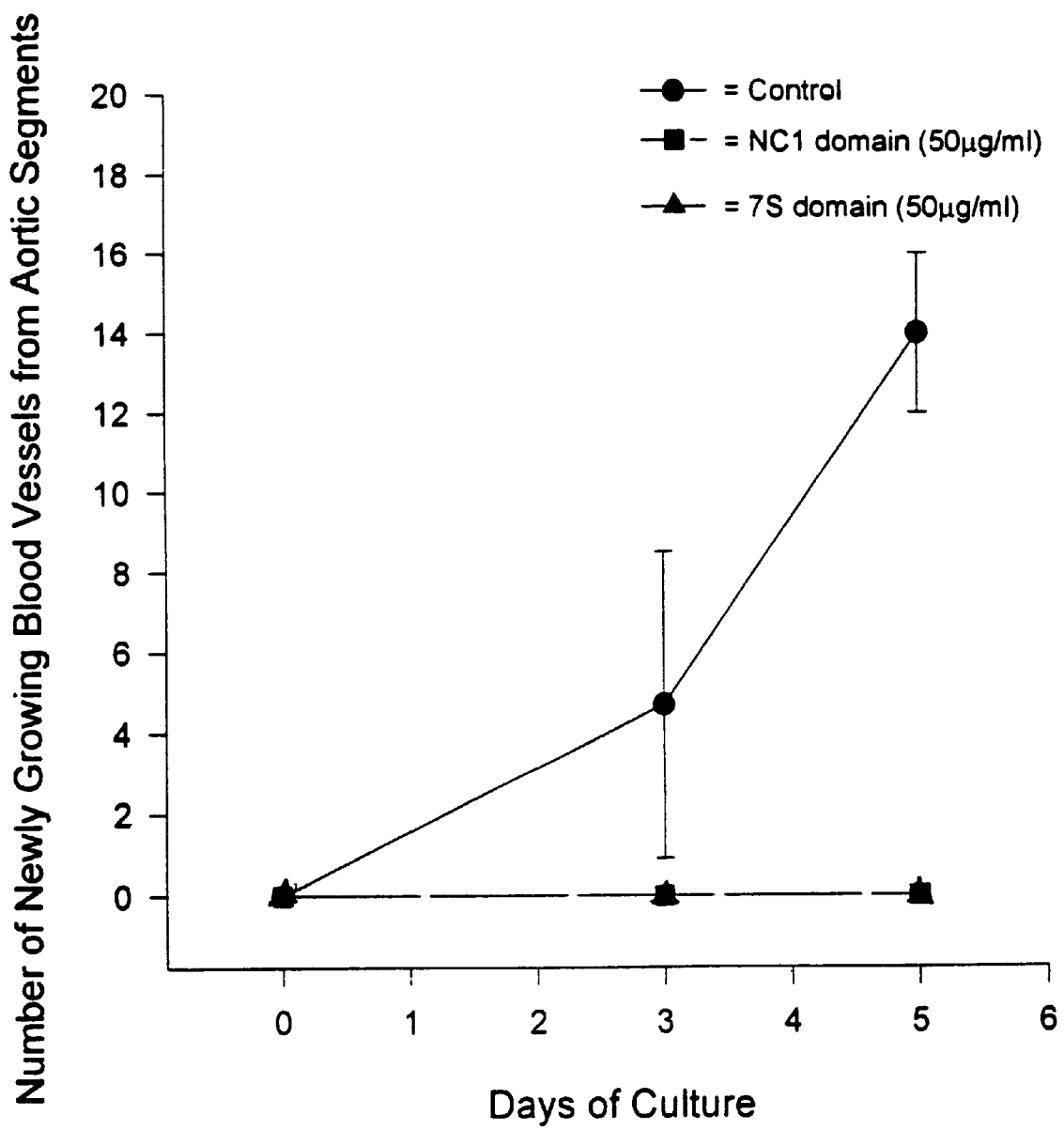
FIG. 7 illustrates the effects of NC1 (Hexamer) and 7S domains of Type IV collagen at a 50 ug/ml concentration on angiogenesis from mouse thoracic aorta organ cultures.
Figure 8:
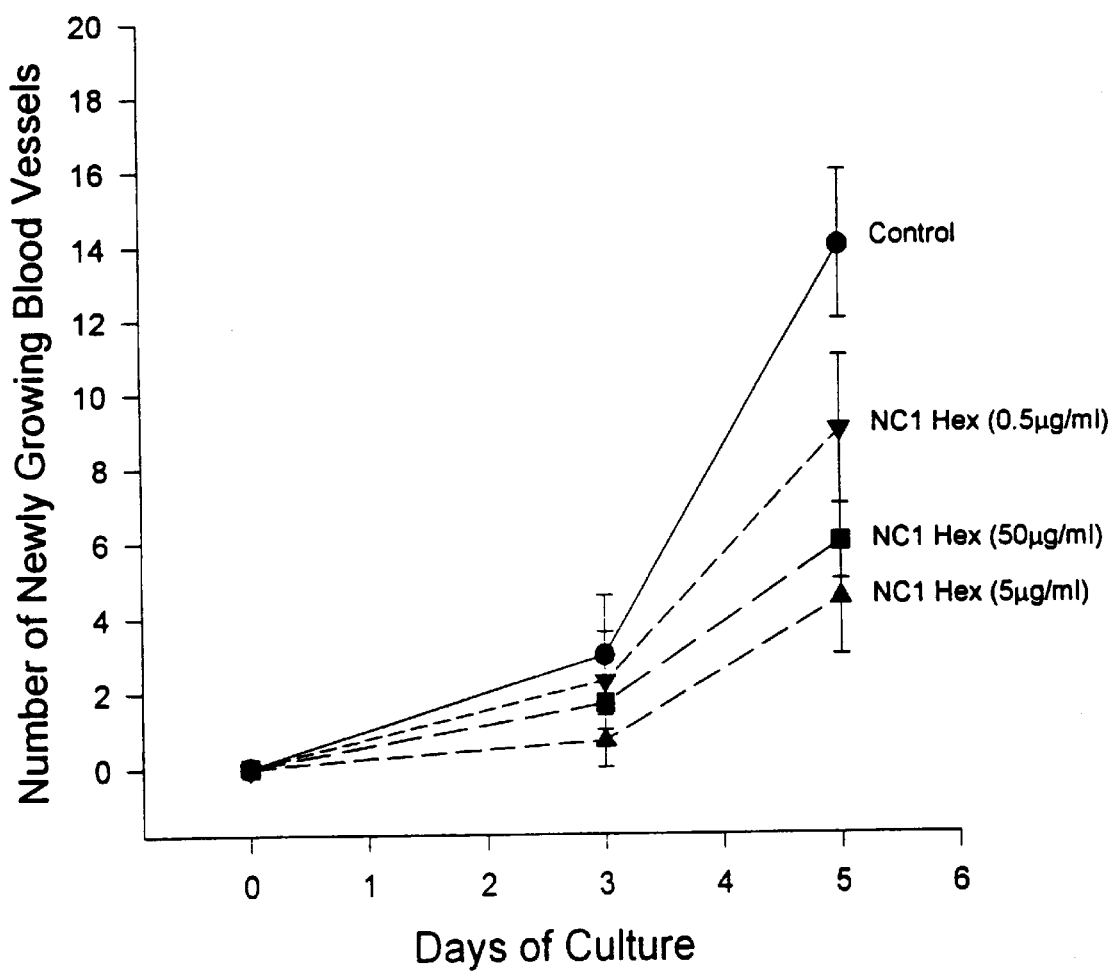
FIG. 8 illustrates the effects of 7S domain of Type IV collagen on angiogenesis from mouse thoracic aorta organ cultures. The domain concentrations employed in this experiment were 0 ug/ml (control); 0.5 ug/ml; 5 ug/ml and 50 ug/ml.
Figure 9:
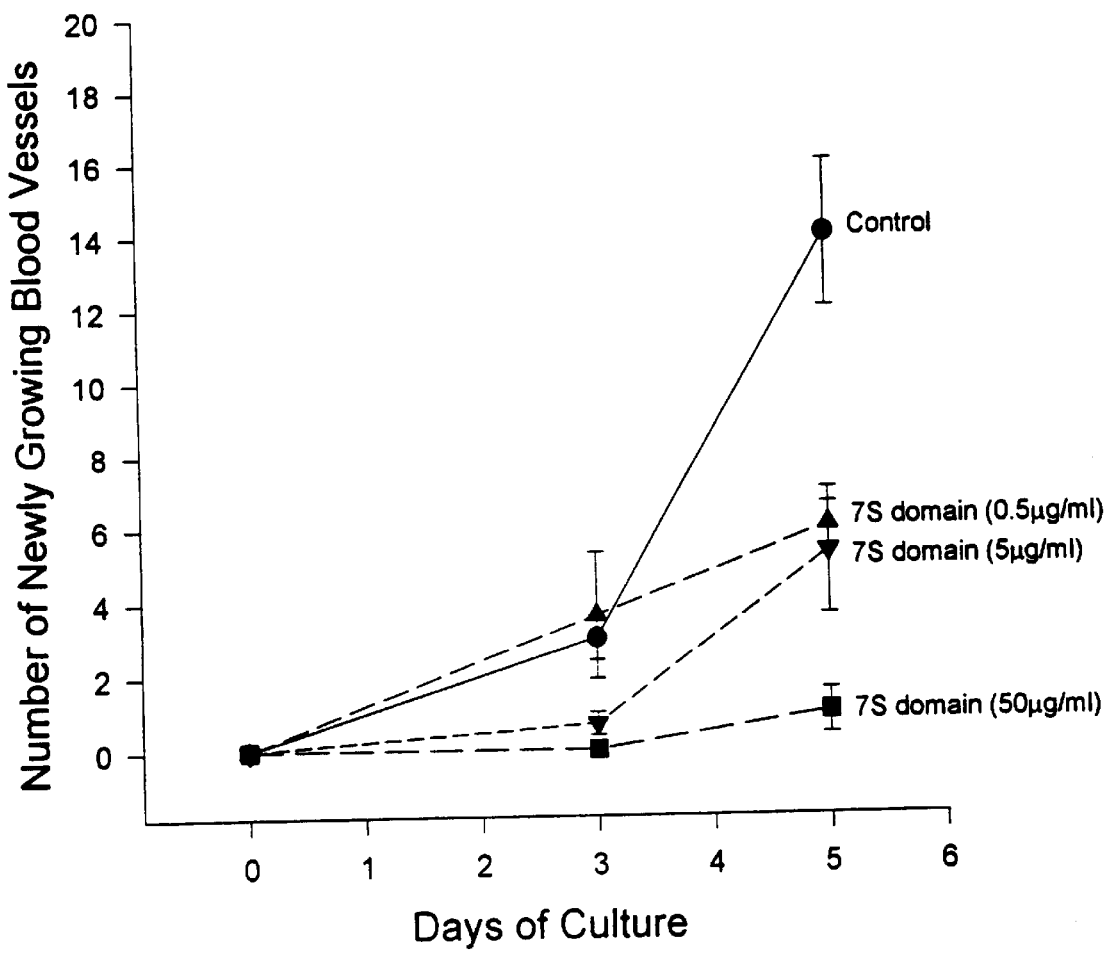
FIG. 9 illustrates the effects of NC1 (Hexamer) domain of Type IV collagen on angiogenesis from mouse thoracic aorta organ cultures. The domain concentrations employed in this experiment were 0 ug/ml (control); 0.5 ug/ml; 5 ug/ml and 50 ug/ml.

After establishing the time course of angiogenesis under control conditions (Matrigel plus MCDB 131 growth medium), experiments were performed using various concentrations of Type IV collagen (isolated from bovine lens) NC1 (hexamer) and 7S domains. Data represents the analysis of at least 3 specimens per experimental condition. In the first experiment (FIG. 7), analysis indicated that a concentration of 50 micrograms/ml, NC1 domain and 7S domain significantly inhibited angiogenesis as monitored at 3 and 5 days of culture. In the second experiment, various concentrations of these domains were analyzed. As indicated in FIG. 8, 7S domain at 50 micrograms/ml again significantly inhibited angiogenesis at 3 and 5 days. Inhibition was reduced at 5 and 0.5 microgams/ml concentrations. As indicated in FIG. 9, NC1 domain was less effective in blocking angiogenesis as compared to that observed in the first experiment (FIG. 7). In addition, as compared to the 7S domain, there was less of a correlation between concentration and inhibitory action.

FIG. 10 are photographs of mouse thoracic aorta segments embedded in Matrigel (EHS basement membrane matrix, Collaborative Biomedical Products, Bedford, Mass.) at 5 days of culture in the presence or absence of 50 ug/ml of Type IV collagen domains. The control specimen (no domains) exhibited growth of microvessels from the cultured tissue into the matrix (FIG. 10A). In contrast, angiogenesis inhibition was observed in tissues cultured in the presence of 50 ug/ml of 7S domain (FIG. 10B) and NC1 (Hexamer) domain (FIG. 10C).

The results of these experiments suggest that as observed previously with Hydra cell aggregates, the 7S domain of Type IV collagen is more effective as a blocking agent as compared to the NC1 domain.

In summary, the present invention is broadly applicable to a variety of in vivo and in vitro uses which include inhibition of metastasis, control of cell division, reduction of scar tissue formation, intervention in epithelial tissue formation, inhibition of angiogenesis, reduction of complications due to cell adhesion in organ transplants, inhibition of angiogenic invasion of tissue, the inhibition of lymphocyte adhesion and mobility, and the maintenance of pluripotent cell isolates in vitro while inhibiting morphological changes and differentiation.

In practicing the invention, the amount or dosage range of NC1 (Hexamer) and 7S domain of Type IV collagen employed is one that effectively inhibits or disrupts cell adhesion to extracellular matrix components or the formation of factional basal lamina. An inhibiting amount of Type IV collagen domain that can be employed ranges generally between about 0.1 and about 500 ug/ml, preferably rang between about 0.5 and about 50 ug/ml.

While the fundamental novel features of the invention has been shown and described, it will be understood that various omissions, substitutions and changes in the form and details illustrated may be made by those skilled in the art without departing from the spirit of the invention. It is the intention, therefore, to be limited only as indicated by the scope of the following claims.

What we claim is:

1. A method for inhibiting basal lamina membrane formation in cell or tissue development comprising contacting the cell or tissue with an effective inhibiting amount of an antibody composition comprising an isolated antibody against a type IV collagen NC1 chain monomer selected from the group consisting of an NC1 α1 chain monomer and an NC1 α2 chain monomer.

2. The method of claim 1 wherein the type IV collagen NC1 chain monomer is the NC1 α2 chain monomer.

3. A method for disrupting basal lamina contact formation with cells or tissues comprising contacting the cells or tissues with an effective inhibiting amount of an antibody composition comprising an isolated antibody against type IV collagen NC1 chain monomer selected from the group consisting of an NC1 α1 chain monomer and an NC1 α2 chain monomer.

4. The method of claim 3 wherein the type IV collagen NC1 chain monomer is the NC1 α2 chain monomer.

5. A method for inhibiting angiogenesis in tissue comprising contacting said tissue with an effective inhibiting amount of an antibody composition comprising an isolated antibody against type IV collagen NC 1 chain monomer selected from the group consisting of an NC1 α1 chain monomer and an NC1 α2 chain monomer.

6. The method of claim 5 wherein the type IV collagen NC1 chain monomer is the NC1 α2 chain monomer.

7. A method for inhibiting tumor-induced angiogenesis in tissue comprising contacting said tissue with an effective inhibiting amount of an antibody composition comprising an isolated antibody against type IV collagen NC1 chain monomer selected from the group consisting of an NC 1 α1 chain monomer and an NC1 α2 chain monomer.

8. The method of claim 7 wherein the type IV collagen NC1 chain monomer is the NC1 α2 chain monomer.

9. The method of claim 1 wherein the type IV collagen NC1 chain monomer is the NC1 α1 chain monomer.

10. The method of claim 3 wherein the type IV collagen NC1 chain monomer is the NC1 α1 chain monomer.

11. The method of claim 5 wherein the type IV collagen NC1 chain monomer is the NC1 α1 chain monomer.

12. The method of claim 7 wherein the type IV collagen NC1 chain monomer is the NC1 α1 chain monomer.

* * * * *